United States Patent
Vaiarello et al.

(10) Patent No.: US 11,883,674 B2
(45) Date of Patent: Jan. 30, 2024

(54) POWER REGULATION OF A COCHLEAR IMPLANT SYSTEM

(71) Applicant: Oticon Medical A/S, Smørum (DK)

(72) Inventors: Yannick Vaiarello, Vallauris (FR);
Taoufik Berbouchi, Vallauris (FR);
Tristan Vincent, Vallauris (FR)

(73) Assignee: Oticon Medical A/S, Smørum (DK)

( * ) Notice: Subject to any disclaimer, the term of this patent is extended or adjusted under 35 U.S.C. 154(b) by 184 days.

(21) Appl. No.: 17/506,845

(22) Filed: Oct. 21, 2021

(65) Prior Publication Data
US 2022/0134114 A1   May 5, 2022

(30) Foreign Application Priority Data

Nov. 3, 2020   (EP) .................................... 20205402

(51) Int. Cl.
*A61N 1/37*   (2006.01)
*A61N 1/378*   (2006.01)
*A61N 1/05*   (2006.01)

(52) U.S. Cl.
CPC ........... *A61N 1/378* (2013.01); *A61N 1/0541* (2013.01)

(58) Field of Classification Search
CPC .... A61N 1/378; A61N 1/3787; A61N 1/0541; A61N 1/36036–36039
See application file for complete search history.

(56) References Cited

U.S. PATENT DOCUMENTS

| | | | |
|---|---|---|---|
| 4,207,441 A | 6/1980 | Ricard et al. | |
| 4,532,930 A | 8/1985 | Crosby et al. | |
| 5,735,887 A * | 4/1998 | Barreras, Sr. | A61N 1/3787 128/903 |
| 6,415,186 B1 * | 7/2002 | Chim | A61N 1/3787 607/57 |
| 9,717,907 B2 * | 8/2017 | Karunasiri | A61N 1/3787 |
| 2011/0009924 A1 * | 1/2011 | Meskens | A61N 1/36038 607/57 |
| 2016/0220818 A1 * | 8/2016 | Karunasiri | A61N 1/3787 |
| 2018/0262037 A1 | 9/2018 | Meskens | |

FOREIGN PATENT DOCUMENTS

| | | |
|---|---|---|
| EP | 3 086 841 A1 | 11/2016 |
| WO | WO 2015/099682 A1 | 7/2015 |

* cited by examiner

*Primary Examiner* — Eric D. Bertram
(74) *Attorney, Agent, or Firm* — Birch, Stewart, Kolasch & Birch, LLP

(57) ABSTRACT

A cochlear implant system is disclosed. The system includes a power management unit that is configured to determine a stimulation power consumption of the implantable unit for providing the plurality of stimulation pulses of the stimulation frame to the auditory nerve fibers of the recipient. The determine of the stimulation power consumption of the implantable unit may be based on the plurality of stimulation pulses determined by the external unit, and more specifically, determined by a sound processor arranged within the external unit and/or the implantable unit. The plurality of stimulation pulses may be communicated to the power management unit. Furthermore, the power management unit may be configured to determine a power consumption stage of the implantable unit.

19 Claims, 4 Drawing Sheets

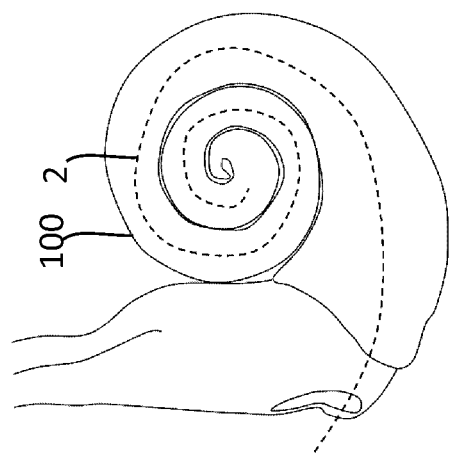
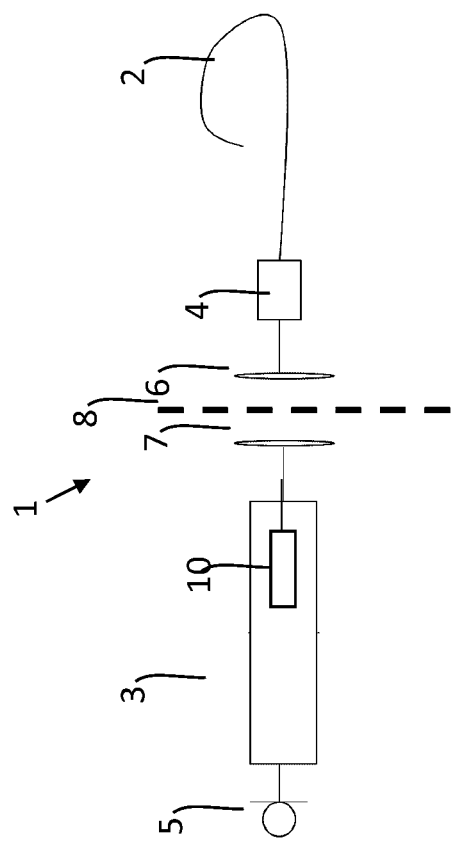
FIG. 1A
FIG. 1B

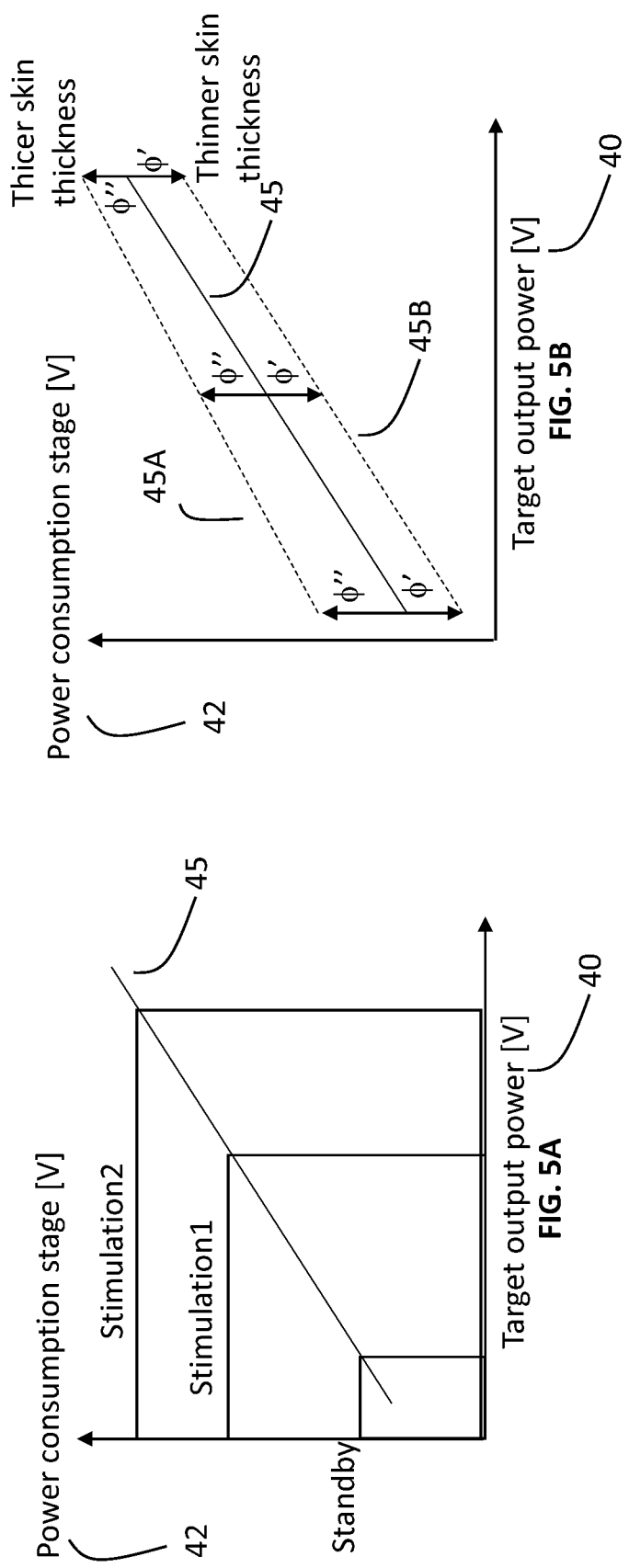

POWER REGULATION OF A COCHLEAR IMPLANT SYSTEM

FIELD

The present disclosure relates to a cochlear implant system and a method for a cochlear implant system. More particularly, the disclosure relates to such system/method provided with a power management unit configured for determining a power consumption of an implantable unit and determine a target power to be transmitted from an external unit to the implantable unit based on at least the determined power consumption.

BACKGROUND

Cochlear implant systems (CIs) are devices containing electrodes inserted in the inner ear (the cochlea) to recover the sensation of audition to people suffering from severe to profound hearing loss. CIs are bypassing most of the functional hearing chain, and generate series of electrical pulse train inside the cochlea to initiate action potentials from the hair cells. Those devices are thus mostly considered as biocompatible electronic machines. Depending on their implementation, they can be either totally implanted, either composed of two main parts. An external unit is the sound processor, often placed near the ear. It contains microphones that capture the environmental sound, which is processed in real time into a series of codes usable by an implantable unit, implanted into the patient. The implantable unit receives both power and sound information though a transcutaneous link from the sound processor, and generates electrical pulses sent into the cochlea via a plurality of electrodes inside the cochlea.

Power transmitted to the implantable unit which is not being used for providing stimulation results in heat and unnecessary lowering of the battery lifetime. Thereby, there is a need for ensuring that enough power is transmitted to the implantable unit for enabling proper functions while keeping the power loss as low as possible.

SUMMARY

According to an aspect of the present disclosure, a cochlear implant system is disclosed. The system includes an external unit configured to be arranged on a head of a recipient or at an ear of the recipient of the cochlea implant system, and the external unit includes at least a first inductive transceiver configured to transmit power via a transcutaneous link. The external unit may be a behind-the-ear hearing aid configured to be arranged behind an ear of the recipient of the cochlear implant system. The system further includes an implantable unit that is configured to be arranged between the skin and the skull of the recipient. The implantable unit may be arranged partly within an ear of the recipient and partly on the skull of the recipient. The implantable unit includes at least an electrode array that includes a plurality of electrodes configured to apply a plurality of stimulation pulses during a stimulation frame to auditory nerve fibers of a recipient of the cochlea implant system, and a second inductive transceiver configured to receive power via the transcutaneous link. Furthermore, the system includes a microphone unit configured to receive an acoustic wave and provide an audio signal based on the acoustic wave, and wherein the plurality of stimulation pulses is determined based on the audio signal. The microphone unit may include one or more microphones which is arranged within the external unit and/or the implantable unit.

The system includes one or more batteries, and for improving the battery lifetime the system includes a power management unit. The power management unit may be configured to determine a stimulation power consumption of the implantable unit for providing the plurality of stimulation pulses of the stimulation frame to the auditory nerve fibers of the recipient. The determine of the stimulation power consumption of the implantable unit may be based on the plurality of stimulation pulses determined by the external unit, and more specifically, determined by a sound processor arranged within the external unit and/or the implantable unit. The plurality of stimulation pulses may be communicated to the power management unit. Furthermore, the power management unit may be configured to determine a power consumption stage of the implantable unit.

The power management unit may be configured to receive input information from other units arranged within the external unit and/or the implantable unit, and wherein the power consumption stage may be determined based on the input information. The power consumption of the implantable unit may vary according to selected coding strategy for determining the plurality of stimulation pulses, the type of the transceivers, the lifetime of the battery or the battery capacity, the type of the implantable unit, whether there are other units within the implantable unit that are needed to be activated during stimulation and/or during a period of time which does not imply stimulation of the auditory nerve fibers. The other units may be sensors, the microphone units, the sound processor and the memory unit.

The power management unit further determines, based on the power consumption stage and a power tuning function, a target output power of the first inductive transceiver for obtaining a target power at the second inductive transceiver which leads to an input power to a stimulator unit of the implantable unit, where the input power is equal to or about equal to the determined stimulation power consumption, and wherein the stimulator unit may be configured to transmit the plurality of the stimulation pulses to the electrode array based on the input power.

The power tuning function may be determined during activation of the external unit or the implantable unit when the external unit is arranged on the head of the recipient or at the ear of the recipient; and thereby, the power tuning function has taken into account a skin thickness of the recipient when determine a plurality of target output powers for different power consumption stage.

According to the power consumption stage of the implantable unit, the power management unit may then be configured to determine the target output power by selecting one of the plurality of target output powers where the power consumption stage matches one of the different power consumption stage. In a situation where the power consumption stage does not match one of the different power consumption stages, the power management unit may be configured to determine the target output power by extracting via linear interpolation of the plurality of target output power as a function of the plurality of power consumption stages.

The power tuning function may include a plurality of target output powers of the first inductive transceiver for different power consumption stages of the implantable.

A power consumption stage may be determined based on the input information, and the input information may include current levels, voltage levels and/or power levels, and thereby, the power consumption stage may include a total current level, or a total voltage level, or a total power level needed for driving the implantable unit optimally during or not during the stimulation frame.

Alternatively, the power tuning function may be determined during a fitting procedure of the cochlear implant system to the recipient; or during manufacturing of the cochlear implant system. During manufacturing of the cochlear implant system, the power tuning function does not take into account the skin thickness of the recipient, and thereby, it may be needed for adapting the power tuning function to the skin thickness of the recipient by applying a tuning factor to the power tuning function. The tuning factor is applied to the power tuning function, such that the determined target output power is turned to fit the skin thickness of the recipient.

The first inductive transceiver may be configured to transmit the target output power to the second inductive transceiver, and result, is a power optimized cochlear implant system, where unwanted reduction of the battery lifetime due to an overestimated power transmission to the implantable unit is avoided.

The plurality of stimulation pulses is communicated to the power management unit, and where each of the plurality of stimulation pulses has a first on-off ratio. During the stimulation frame where the plurality of stimulation pulses is applied to the auditory nerve fibers, each of the plurality of stimulation pulses has a second on-off ratio. A pre-target output power may then be determined based on the power consumption stage and the power tuning function, and the target output power may then be determined by multiplying to the pre-target output power a ratio between the first on-off ratio and the second on-off ratio. Thereby, the target output power is more precisely estimated.

The implantable unit may include a stimulator unit configured to transmit the plurality of stimulation pulses to the electrode array. Whenever the stimulator unit is powered up, the stimulator unit consumes a standby current. The determine of the stimulation power consumption may include determine the standby current and estimate a stimulation current for each of the stimulation pulse of the plurality of stimulation pulses; and wherein the stimulation power consumption includes the standby current and the stimulation current for each of the stimulation pulses of the plurality of stimulation pulses. Additional currents may be added depending on other activities of the stimulator unit.

Furthermore, the determine of the stimulation power consumption includes determine a polarization current for each of the stimulation pulse of the plurality of stimulation pulses, and where the polarization current may be depended on a current amplitude of the stimulation pulse of the plurality of stimulation pulses, and wherein the stimulation power consumption includes the standby current, stimulation current and the polarization current for each of the stimulation pulses of the plurality of stimulation pulses.

Alternatively, the stimulation power consumption may include the standby current and an average of the stimulation current of each of the plurality of stimulation pulses, and/or an average of the polarization current of each of the plurality of stimulation pulses.

The input information may be transmitted to the power management unit by a sound processor arranged in either the external unit and/or the implantable unit. The sound processor may be configured to process the audio signal and provide the plurality of stimulation pulses based on the audio signal and a coding strategy, and where the input information includes information about the selected coding strategy, about a signal-to-noise ratio of the audio signal, and/or about whether the audio signal relates to a voice speech or a none-voice speech. In one example, a pulse rate, a pulse amplitude or a pulse width of the plurality of stimulation pulses may vary according to the coding strategy, the signal-to-noise ratio of the audio signal, and/or whether the audio signal relates to a voice speech or a none-voice speech, and thereby, the stimulation power consumption varies along with the variation of the pulse rate, the pulse amplitude and/or the pulse width. Therefore, a more precise estimation of the target output power is obtained, and which results in an improved battery lifetime as overestimation of needed power transmitted to the implantable unit is reduced significantly.

The input information may be transmitted to the power management unit by the first and/or second inductive transceiver, where the input information includes information about the type of the inductive transceiver, and/or about a resonance frequency of the inductive transceiver. In one example, if the power management unit is applied into the external unit, and an upgrade of the second inductive transceiver is performed, the power management unit may be configured to determine the target output power at the first inductive transceiver without doing any further fitting of the cochlear implant system to the recipient. The input information from the second inductive transceiver may include information about a supply voltage of the transceiver, and/or a version number of the upgraded transceiver, where the version number is used for extracting from the memory unit of the cochlear implant system a supply voltage needed for the second inductive transceiver to drive.

The input information may be transmitted to the power management unit by a battery, where the input information may include information about a battery lifetime of the battery or a battery capacity. In one example, when the battery capacity is low the power management unit is configured to reduce the determined stimulation power consumption by selecting a group of the plurality of stimulation pulses to be transmitted to the implantable unit. The selection of the stimulation pulses into the group is done based on an importance level of each of the plurality of stimulation levels. The importance level is determined by the sound processor, and which is determined based on the signal to noise ratio of the stimulation pulse, whether the stimulation pulse contains a voice speech or a none voice speech, a pulse amplitude or a pulse width of the stimulation pulse.

The input information may be transmitted to the power management unit by the implantable unit, where the input information may include information about the type of the implantable unit and/or about power consumption of the implantable unit outside the stimulation frame. In one example, if the power management unit is applied into the external unit, and an upgrade of the implantable unit is performed, the power management unit may be configured to determine the target output power at the first inductive transceiver without doing any further fitting of the cochlear implant system to the recipient. The input information from the implantable unit may include information about units within the implantable unit, such as different supply voltages of the transceiver, the stimulator, the microphone, the sensor, the sound processor, the memory unit, another power management unit all arranged within the implantable unit. Beside the different supply voltage, version numbers may be informed to the power management unit arranged within the external unit.

The input information may be transmitted to the power management unit by the memory unit, where the input information includes information about a skin thickness of the recipient of the system, and/or about the type of the inductive transceiver, and/or about the resonance frequency of the inductive transceiver, and/or about the coding strategy.

The input information and the plurality of stimulation pulses may be communicated to the power management unit during one or more communication frames, and each of the one or more communication frames includes a plurality of electrical pulses representing the input information for the power management unit and the plurality of stimulation pulses.

The plurality of stimulation pulses is communicated to the power management unit, and where each of the plurality of stimulation pulses has a first on-off ratio. During the stimulation frame where the plurality of stimulation pulses is applied to the auditory nerve fibers, each of the plurality of stimulation pulses has a second on-off ratio. A pre-target output power may then be determined based on the power consumption stage and the power tuning function, and the target output power may then be determined by multiplying to the pre-target output power a ratio between the first on-off ratio and the second on-off ratio. Thereby, the target output power is more precisely estimated.

The cochlear implant system may comprise another power management unit arrange within the implantable unit, and wherein the another power management unit may be configured to distribute power to at least the electrode array. The another power management unit is configured to transfer input information to the power management unit of the external unit when receiving a command from the power management unit of the external unit.

BRIEF DESCRIPTION OF DRAWINGS

Aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects.

These and other aspects, features and/or technical effect will be apparent from and elucidated with reference to the illustrations described hereinafter in which:

FIGS. 1A and 1B illustrate a cochlear implant system;

FIGS. 5A and 5B illustrate an example of the power tuning function.

DETAILED DESCRIPTION

Figure 2:
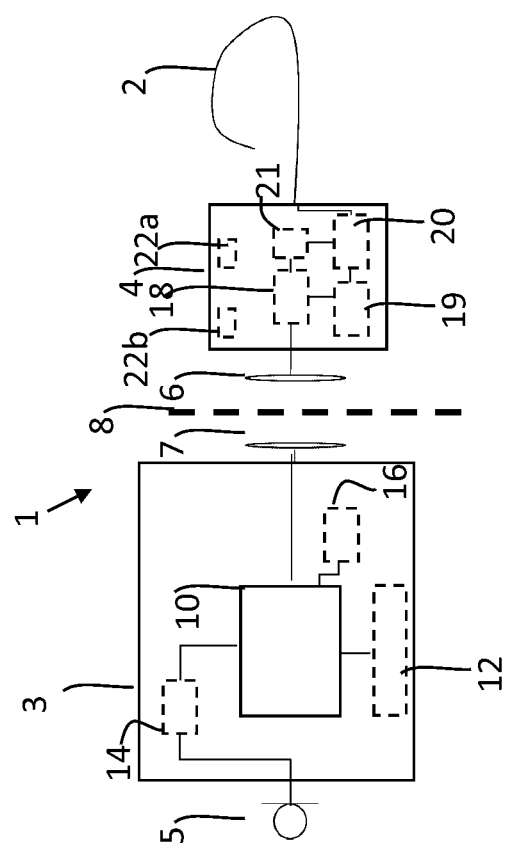
FIG. 2 illustrate another example of the cochlear implant system.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements").

Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

A "cochlear implant system" represents a particular type of a "hearing system" comprising an external unit, which receives acoustic sound and processes the acoustic sound into a coded audio, and an implantable unit which receives the coded audio signal.

Now referring to FIG. 1A, it is illustrating a cochlear implant system 1 that comprises an external unit 3, a microphone unit 5, a power management unit 10, a first inductive transceiver 7, an implantable unit 4, an electrode array 2 a stimulator unit 20, and a second inductive transceiver 6. In this specific example, the external unit 3 is configured to be arranged on a head of a recipient or at an ear of the recipient of the cochlea implant system. The external unit includes at least the first inductive transceiver 7 configured to communicate power and/or data via a transcutaneous link that goes through the skin 8 of the recipient and to the second inductive transducer that is arranged within the implantable unit 4. The implantable unit 4 is connected to the electrode array 2. In FIG. 1B, it is illustrated that the electrode array 2 is inserted into the cochlea 100 of the recipient. The electrode array 2 includes a plurality of electrodes configured to apply a plurality of stimulation pulses during a stimulation frame to the auditory nerve fibers of the cochlea. The external unit 3 includes a microphone unit 5 configured to receive an acoustic wave and provide an audio signal based on the acoustic wave, and wherein the plurality of stimulation pulses is determined based on the audio signal. Furthermore, in this specific example, the external unit 3 comprises the power management unit 10 which is configured to determine a target output power to be transmitted by the first inductive transceiver 7 for obtaining a target power at the second inductive transceiver which leads to an input power to the stimulator unit 20 of the implantable unit 4, where the input power is equal to or about equal to the determined stimulation power consumption, and wherein the stimulator unit 20 is configured to transmit the plurality of the stimulation pulses to the electrode array 2 based on the input power.

the electrode array which is equal to or about equal to a determined stimulation power consumption. Furthermore, the target power leads to a first input power to the electrode array which is equal to or about equal to the determined stimulation power consumption and a second input power for driving the implantable unit.

More specifically, the power management unit 10 is configured to determine the stimulation power consumption of the implantable unit 4 for providing the plurality of stimulation pulses of the stimulation frame to the auditory nerve fibers of the recipient. Thus, a power consumption stage of the implantable unit is determined, and based on the power consumption stage and a power tuning function, the target output power of the first inductive transceiver is determined for obtaining the target power at the second inductive transceiver which leads to an input power to the stimulator unit 20 of the implantable unit 4, where the input power is equal to or about equal to the determined stimulation power consumption, and wherein the stimulator unit 20 is configured to transmit the plurality of the stimulation pulses to the electrode array 2 based on the input power.

In another example of the cochlear implant system the external unit 3 and the implantable unit 4 are replaced by a fully implantable unit which comprises the microphone unit 5, the power management unit 10, the electrode array 2 and a first inductive transceiver 7 configured to communicate via the transcutaneous link to an external device.

FIG. 2 illustrates another example of the cochlear implant system 1. The cochlear implant system 1 comprises an external unit 3, a microphone unit 5, a power management unit 10, a first inductive transceiver 7, a sound processor 14, a memory unit 12, an implantable unit 4, an electrode array 2, a second inductive transceiver (6,18), a stimulator unit 20, and optionally, another power management unit 19, a demodulator 20 and a battery 16

The power management unit 10 is configured to determine the power consumption stage based on input information from other units (6, 7, 12, 14, 16, 18, 19, 20, 21, 22*a* and 22*b*) arranged within the external unit 3 and/or the implantable unit 4. The sound processor 14 is configured to process the audio signal and provide the plurality of stimulation pulses based on the audio signal and a coding strategy, and where the input information includes information about the selected coding strategy, about a signal-to-noise ratio of the audio signal, and/or about whether the audio signal relates to a voice speech or none-voice speech.

The first and/or second inductive transceiver (6,7,18) may transmit input information to the power management unit 10, where the input information includes information about the type of the inductive transceiver (6,7,18), and/or about a resonance frequency of the inductive transceiver (6,7,18).

The power management unit may be configured to determine a battery lifetime and a battery capacity of the battery 16. The input information from the battery 16 to the power management unit 10 comprises battery voltages, where the power management unit 10 is configured to determine the battery lifetime and the battery capacity based on the battery voltages received from the battery 16.

The implantable unit 4 is configured to transmit input information to the power management unit 10 which includes information about the type of the implantable unit 4 and/or about power consumption of the implantable unit 4 outside the stimulation frame.

The external unit 3 includes the memory unit 12 which is configured to transmit information about a skin thickness of the recipient, type of the inductive transceiver (6,7,18), a resonance frequency of the inductive transceiver (6,7,18) and/or the coding strategy on request by the power management unit 10. The power management unit 10 is configured to request the input information from the memory unit 12 during booting or activation of the external unit 3 and/or the implantable unit 4.

The first inductive transceiver 7 transmits the target output power and a HF signal to the second inductive transceiver 6. The second inductive transceiver 18 is then configured to forward the HF signal to the demodulator 21 and a target power to the another power management unit 19. The target power is equal to the target output power times a loss coefficient which is mainly depended on the skin thickness of the recipient. The demodulator 21 is then configured to demodulate the HF signal into the plurality of stimulation pulses and transmit the plurality of stimulation pulses to the stimulator unit 20. The another power management unit 19 is configured to supply the stimulator unit 20 with an input power that comes from the target power. The stimulator unit 20 is then configured to transmit the plurality of stimulation pulses to the electrode array 2 based on the input power.

In this specific example, in FIG. 2, the power tuning function which is used for determining the power consumption stage is stored in the memory unit 12. Furthermore, the stimulation power consumption is determined based on the plurality of stimulation pulses which is received from the sound processor 14.

Figure 3:
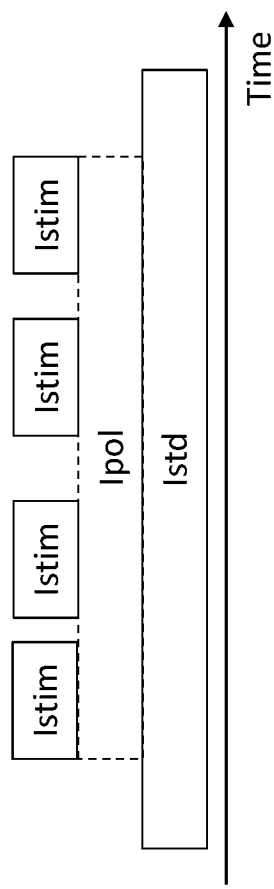
FIG. 3 illustrate the determination of the stimulation power consumption.

FIG. 3 illustrates the determination of the stimulation power consumption which in this example includes a standby current (Istd) consumed by the stimulator unit 20 of the implantable unit 4 during up powering of the implantable unit 4, and a stimulation current (Istim) for each of the stimulation pulse of the plurality of stimulation pulses.

Alternatively, the stimulation power consumption further includes a polarization current (Ipol) for each of the stimulation pulse of the plurality of stimulation pulses, and where the polarization current is depended on a current amplitude of the stimulation pulse of the plurality of stimulation pulses.

The stimulation power consumption may include the standby current (Istd) and an average of the stimulation current (Istim) of each of the plurality of stimulation pulses, and/or an average of the polarization (Ipol) current of each of the plurality of stimulation pulses.

Figure 4:
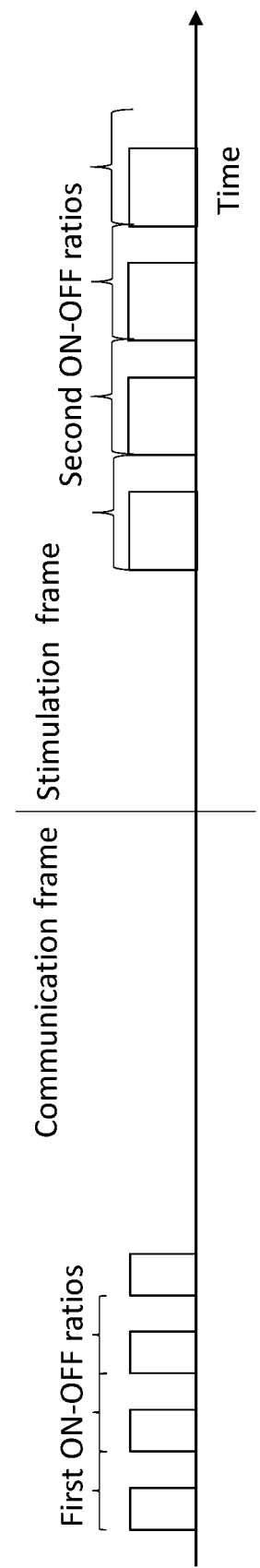
FIG. 4 illustrates a specific situation of a power management unit.

FIG. 4 illustrates a situation where the power management unit 10 receives input information as electrical pulses and/or the plurality of stimulation pulses during a communication frame where each electrical pulse and each of the plurality of stimulation pulses has a first on-off ratio. During the stimulation frame where the plurality of stimulation pulses is transmitted to the electrode array 2, each of the plurality of stimulation pulses has a second on-off ratio which is larger than the first on-off-ratio. A pre-target output power may then be determined based on the power consumption stage and the power tuning function, and the target output power may then be determined by multiplying to the pre-target output power a ratio between the first on-off ratio and the second on-off ratio. Thereby, the target output power is more precisely estimated.

FIGS. 5A and 5B illustrate an example of the power tuning function 45. FIG. 5A illustrate the power tuning function 45 that includes a relation between a plurality of target output powers 40 of the first inductive transceiver 7 for different power consumption stages 42 of the implantable unit 4. For example, in FIG. 5A it is illustrated for three different situations where a target output power 40 is extracted. One of the situations is where the implantable unit is powered up and in standby mode, and in this situation the power consumption stage is "standby". Two other situations are shown, i.e. "stimulation 1" and "stimulation 2", respectively, and both situations relate to when the electrode array stimulates the auditory nerve fibers. The reason for the different target output power 40 for the two situations, i.e. "stimulation 1" and "stimulation 2", may for example be to different coding strategies in the two situations, or different characteristics of the audio signal for which the plurality of stimulation pulses is based on. The different characteristics could for example be different signal-to-noise ratio, or whether in "situation 1" the audio signal relates to a voice speech, and in "situation 2", the audio signal relates to a none-voice speech.

FIG. 5B illustrates an example where the power tuning function 45 is adapted to a skin thickness of a recipient of the cochlear implant system via a tuning factor ($\phi'$, $\phi''$). In this example, the power tuning function 45B is downscaled by the tuning factor ($\phi'$) due to a thinner skin thickness of the recipient of the cochlear implant system 1. Alternatively, the power tuning function 45A is upscaled by the tuning factor ($\phi''$) due to a thicker skin thickness, but in the upscaled power tuning function 45A the gradient has changed due to for example a different type of the second inductive transceiver 6, or a different type of the implantable unit or the external unit.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

In still a further aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

The above described method, including all corresponding exemplary embodiments, for a cochlear implant system may be implemented in software.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

In another aspect, a data processing system is disclosed comprising a processor adapted to execute the computer program for causing the processor to perform at least some (such as a majority or all) of the steps of the method described above and in the claims.

As already outlined above, the above described method, including all corresponding exemplary embodiments, for a cochlear implant system may be implemented in software.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A cochlear implant system comprising:
an external unit configured to be arranged on a head of a recipient or at an ear of the recipient of the cochlea implant system, the external unit including at least:
a first inductive transceiver configured to transmit power via a transcutaneous link,
an implantable unit configured to arranged between the skin and the skull of the recipient, the implantable unit including at least:
an electrode array including a plurality of electrodes configured to apply a plurality of stimulation pulses during a stimulation frame to auditory nerve fibers of a recipient of the cochlea implant system, and
a second inductive transceiver configured to receive power via the transcutaneous link,
a microphone unit configured to receive an acoustic wave and provide an audio signal based on the acoustic wave, wherein the plurality of stimulation pulses is determined based on the audio signal;
a power management unit configured to:
determine a stimulation power consumption of the implantable unit for providing the plurality of stimulation pulses of the stimulation frame to the auditory nerve fibers of the recipient,
determine a power consumption stage of the implantable unit, and
determine, based on the power consumption stage and a power tuning function, a target output power of the first inductive transceiver for obtaining a target power at the second inductive transceiver which leads to an input power to a stimulator unit of the implantable unit, where the input power is equal to or about equal to the determined stimulation power consumption, and
wherein the stimulator unit is configured to transmit the plurality of the stimulation pulses to the electrode array based on the input power,
wherein determining the stimulation power consumption includes:
determining a standby current consumed by the stimulator unit of the implantable unit during up powering of the implantable unit; and
estimating a stimulation current for each of the stimulation pulse of the plurality of stimulation pulses, and
wherein the stimulation power consumption includes the standby current and the stimulation current for each of the stimulation pulses of the plurality of stimulation pulses.

2. A cochlear implant system according to claim 1, wherein determining the stimulation power consumption includes:

determining a polarization current for each of the stimulation pulse of the plurality of stimulation pulses, the polarization current depending on a current amplitude of the stimulation pulse of the plurality of stimulation pulses, and wherein the stimulation power consumption includes the standby current, stimulation current and the polarization current for each of the stimulation pulses of the plurality of stimulation pulses.

3. A cochlear implant system according to claim 2, wherein the stimulation power consumption includes the standby current and an average of the stimulation current of each of the plurality of stimulation pulses, and/or an average of the polarization current of each of the plurality of stimulation pulses.

4. A cochlear implant system according to claim 2, wherein the power tuning function includes a plurality of target output powers of the first inductive transceiver for different power consumption stages of the implantable.

5. A cochlear implant system according to claim 2, wherein the power consumption stage is determined by receiving input information from other units arranged within the external unit and/or the implantable unit.

6. A cochlear implant system according to claim 1, wherein the stimulation power consumption includes the standby current and an average of the stimulation current of each of the plurality of stimulation pulses, and/or an average of the polarization current of each of the plurality of stimulation pulses.

7. A cochlear implant system according to claim 1, wherein the power tuning function includes a plurality of target output powers of the first inductive transceiver for different power consumption stages of the implantable.

8. A cochlear implant system according to claim 1, wherein the power consumption stage is determined by receiving input information from other units arranged within the external unit and/or the implantable unit.

9. A cochlear implant system according to claim 8, wherein the other units include one or more of following:
- a sound processor configured to process the audio signal and provide the plurality of stimulation pulses based on the audio signal and a coding strategy, the input information including information about the selected coding strategy, about a signal-to-noise ratio of the audio signal, and/or about whether the audio signal relates to a voice speech or none-voice speech;
- the first and/or second inductive transceiver, the input information including information about the type of the inductive transceiver, and/or about a resonance frequency of the inductive transceiver;
- a battery, the input information including information about a battery lifetime of the battery or a battery capacity;
- the implantable unit, the input information including information about the type of the implantable unit and/or about power consumption of the implantable unit outside the stimulation frame;
- a memory unit, the input information including information about a skin thickness of the recipient of the system, and/or about the type of the inductive transceiver, and/or about the resonance frequency of the inductive transceiver, and/or about the coding strategy.

10. A cochlear implant system according to claim 1, wherein the target output power and the stimulation power consumption are determined during one or more communication frames, each of the one or more communication frames including a plurality of electrical pulses representing the input information for the power management unit and the plurality of stimulation pulses.

11. A cochlear implant system according to claim 1, wherein the power tuning function is determined:
- during activation of the external unit or the implantable unit when the external unit is arranged on the head of the recipient or at the ear of the recipient;
- during a fitting procedure of the cochlear implant system to the recipient; or
- during manufacturing of the cochlear implant system.

12. A cochlear implant system according to claim 1, wherein the power tuning function is adapted to a skin thickness of a recipient of the cochlear implant system via a tuning factor.

13. A cochlear implant system according to claim 1, comprising another power management unit arranged within the implantable unit, the another power management unit being configured to distribute power to at least the stimulator unit of the implantable unit, wherein the stimulator unit is connected to the electrode array.

14. A cochlear implant system according to claim 1, wherein the power tuning function is stored in a memory unit arranged in the external unit.

15. A cochlear implant system according to claim 1, wherein the stimulation power consumption is determined based on the plurality of stimulation pulses.

16. A cochlear implant system according to claim 1, wherein the power management unit is arranged within the external unit.

17. A cochlear implant system according to claim 6, wherein the power tuning function includes a plurality of target output powers of the first inductive transceiver for different power consumption stages of the implantable.

18. A cochlear implant system according to claim 1, wherein the power tuning function includes a plurality of target output powers of the first inductive transceiver for different power consumption stages of the implantable.

19. A cochlear implant system according to claim 1, wherein the power consumption stage is determined by receiving input information from other units arranged within the external unit and/or the implantable unit.

* * * * *